United States Patent
Chen et al.

(10) Patent No.: US 11,111,516 B2
(45) Date of Patent: Sep. 7, 2021

(54) **MALR-KNOCKOUT *BACILLUS LICHENIFORMIS* STRAIN, CONSTRUCTION METHOD AND USE**

(71) Applicant: Lifecome Biochemistry Co., Ltd, Fujian (CN)

(72) Inventors: Shouwen Chen, Fujian (CN); Fei Wu, Fujian (CN); Dongbo Cai, Fujian (CN); Bowen Zhang, Fujian (CN); Junhui Li, Fujian (CN); Lijun Lou, Fujian (CN); Xiangqi Qiu, Fujian (CN)

( * ) Notice: Subject to any disclaimer, the term of this patent is extended or adjusted under 35 U.S.C. 154(b) by 0 days.

(21) Appl. No.: 16/970,397

(22) PCT Filed: Aug. 5, 2019

(86) PCT No.: PCT/CN2019/099224
§ 371 (c)(1),
(2) Date: Aug. 17, 2020

(87) PCT Pub. No.: WO2020/029910
PCT Pub. Date: Feb. 13, 2020

(65) Prior Publication Data
US 2021/0095324 A1 Apr. 1, 2021

(30) Foreign Application Priority Data
Aug. 8, 2018 (CN) .......................... 201810898060.8

(51) Int. Cl.
*C12P 21/02* (2006.01)
*C12N 15/75* (2006.01)

(52) U.S. Cl.
CPC .............. *C12P 21/02* (2013.01); *C12N 15/75* (2013.01)

(58) Field of Classification Search
None
See application file for complete search history.

(56) References Cited

U.S. PATENT DOCUMENTS

2010/0064393 A1   3/2010   Berka et al.

FOREIGN PATENT DOCUMENTS

CN           108277191 A        7/2018

OTHER PUBLICATIONS

Subtilisin product information page—Sigma Millipore. Retrieved from < https://www.sigmaaldrich.com/life-science/metabolomics/enzyme-explorer/analytical-enzymes/subtilisin.html > on Jan. 19, 2021.*

* cited by examiner

*Primary Examiner* — Suzanne M Noakes
(74) *Attorney, Agent, or Firm* — Prakash Nama; Global IP Services, PLLC

(57) ABSTRACT

Provided are malR-knockout *Bacillus licheniformis* strain, a construction method and a use. Using a genetic engineering method, gene, namely, the malR gene, which is in charge of conducting the transcription of the carbon metabolism transcription factor MalR, in the genome of *Bacillus licheniformis* DW2 is knocked out, thereby successfully obtaining *Bacillus licheniformis* DW2ΔmalR, from which the malR gene has been deleted. In comparison with *Bacillus licheniformis* DW2, the strain obtained by the construction can improve the Bacitracin yield in a fermentation broth during Bacitracin fermentation by at least 23%.

4 Claims, 5 Drawing Sheets
Specification includes a Sequence Listing.

SEQUENCE LISTING

<160> NUMBER OF SEQ ID NOS: 9

<210> SEQ ID NO 1
<211> LENGTH: 771
<212> TYPE: DNA
<213> ORGANISM: Bacillus licheniformis

<400> SEQUENCE: 1

```
atgcagttgg aagaattaat gaacaagcat tataaaaaat tgaacgaaaa cgactttcat      60
gttttgaaat atattttgaa ccatcaagac acttgctaca agctgggcat caacgaatta     120
gcaaagaaat gcaacgtatc ccgcacatcg attttaaggc tttctcaaaa attggatttc     180
agcgggtaca gcgagttcag ggtgtttctg aaatgggagg ccgagaaacg ggaagaagag     240
cgggaagatt gccgttcctt tgaatgcctc atgagggata tggaagcaag catgaagtat     300
ttgaaaaata cggatttgcg caagatgtgt cagctcattg acgaagcaga ccgcattttt     360
gtctatggtt caggtaccgc tcagaccacg tgcgcttatg agctgcagcg aatgtttgtt     420
tctcagcacc gttatttgac ggtgatcaaa gatcaaatcg atttcgacct catgtttcct     480
gattttagcc cggccgatct gatcatcatc atttcgctgt caggagaaac cccgtcgctg     540
attccgcagg cacagtctct gtcggcaaaa ggcattcctt ttatctcttt gactaatttg     600
aaaaataatc tgctcgccca gctcacgcct tacaatctct atgcgccgag ccagacggtg     660
```

```
acggtttatc caaaaacgga gctgacagct tttgcgccct ttttctcgt tggggaagcg      720 ctgtttcgca gctatgtcga ctatgctgaa gaaagaaaaa atcaggaata a              771
```

<210> SEQ ID NO 2
<211> LENGTH: 28
<212> TYPE: DNA
<213> ORGANISM: Bacillus licheniformis

<400> SEQUENCE: 2

```
cgggatccac ggagcgatcc aaaacttc                                        28
```

<210> SEQ ID NO 3
<211> LENGTH: 41
<212> TYPE: DNA
<213> ORGANISM: Bacillus licheniformis

<400> SEQUENCE: 3

```
agagactgtg cctgcggaat tgtcttgatg gttcaaaata t                         41
```

<210> SEQ ID NO 4
<211> LENGTH: 41
<212> TYPE: DNA
<213> ORGANISM: Bacillus licheniformis

<400> SEQUENCE: 4

```
atattttgaa ccatcaagac aattccgcag gcacagtctc t                         41
```

<210> SEQ ID NO 5
<211> LENGTH: 28
<212> TYPE: DNA
<213> ORGANISM: Bacillus licheniformis

<400> SEQUENCE: 5

```
gctctagaaa ggtcagatag gtggtaag                                        28
```

<210> SEQ ID NO 6
<211> LENGTH: 18
<212> TYPE: DNA
<213> ORGANISM: Bacillus licheniformis

<400> SEQUENCE: 6

```
atgtgataac tcggcgta                                                   18
```

<210> SEQ ID NO 7
<211> LENGTH: 18
<212> TYPE: DNA
<213> ORGANISM: Bacillus licheniformis

<400> SEQUENCE: 7

```
gcaagcagca gattacgc                                                   18
```

<210> SEQ ID NO 8
<211> LENGTH: 20
<212> TYPE: DNA
<213> ORGANISM: Bacillus licheniformis

<400> SEQUENCE: 8

```
gacgcttcca aatacgtatt                                                 20
```

<210> SEQ ID NO 9
<211> LENGTH: 22
<212> TYPE: DNA
<213> ORGANISM: Bacillus licheniformis

```
<400> SEQUENCE: 9
atgataacga caaatgaaga gc                                                      22
```

MALR-KNOCKOUT BACILLUS LICHENIFORMIS STRAIN, CONSTRUCTION METHOD AND USE

BACKGROUND OF THE INVENTION

The present invention relates to the technical field of modifying Bacillus licheniformis strain, and more specifically relates to a malR-knockout Bacillus licheniformis strain, construction method and use thereof.

Bacitracin, is a kind of peptide antibiotics produced by Bacillus subtilis and Bacillus licheniformis, comprising 12 amino acid residues. It has 11 constituent amino acids, comprising ornithine (Orn), D-phenylalanine (D-Phe), isoleucine Histidinse (His), D-aspartic acid (D-Asp), asparagine (Asn), lysine (Lys), D-glutamic acid (D-Glu), cysteine (Cys), leucine (Leu), isoleucine (Ile) and valine (Val). Bacitracin can inhibit or kill certain pathogenic bacteria, and can strongly inhibit the growth of gram-negative bacteria, and has a synergistic enhancement effect when used with other antibiotics (such as penicillin and gentamicin); also, it is virtually not absorbed in the intestinal tracts of animals, and will be excreted quickly leaving no residues, therefore it is widely used as a supplemental substance in animal feeds.

Bacitracin is synthesized by non-ribosomal synthetase using amino acids as precursor substances. The main focus of current researches is the increase in yield of Bacitracin by increasing the supply of several precursor amino acids of Bacitracin, but there are very few literatures on the increase in yield of Bacitracin by modifying transcriptional regulators.

There are many genes in Bacillus licheniformis that are closely related to a synthesis of bacterial strain metabolites. However, it is still unknown which genes are related to the yield of Bacitracin, and it is yet to be studied in detail which genetic modification methods can obtain a high yield rate of Bacitracin engineering bacteria.

BRIEF SUMMARY OF THE INVENTION

One of the objects of the present invention is to provide a construction method of a malR-knockout Bacillus licheniformis strain so as to successfully obtain malR-knockout Bacillus licheniformis strain, wherein malR is a gene of carbon metabolism transcription factor MalR.

A method for constructing malR-knockout Bacillus licheniformis strain comprises the following steps:

(1) using genomic DNA of Bacillus licheniformis DW2 as a template, obtaining an upstream homology arm of the malR gene and a downstream homology arm of the malR gene by PCR (polymerase chain reaction) amplification;

(2) connecting the upstream homology arm of the malR gene and the downstream homology arm of the malR gene by overlap extension PCR to obtain a target gene segment;

(3) performing double digests of the target gene segment by XbaI and BamHI restriction enzymes to obtain a digested gene segment;

(4) preparing plasmid T2(2)-ori, and performing double digests of the plasmid T2(2)-ori by XbaI and BamHI restriction enzymes to obtain a linear plasmid segment;

(5) ligating the digested gene segment obtained in step (3) and the linear plasmid segment obtained in step (4) by DNA ligase to obtain a knockout plasmid T2(2)-ΔmalR;

(6) transforming the knockout plasmid T2(2)-ΔmalR into Bacillus licheniformis DW2, and screening to obtain a positive transformant using kanacillin as a screening marker;

(7) after transferring and culturing the positive transformant for several times at 45° C., performing colony PCR to obtain positive single crossover binder strains that have single crossover between the upstream homology arm of the malR gene/the downstream homology arm of the malR gene and the genomic DNA of Bacillus licheniformis DW2;

(8) selecting the positive single crossover binder strain that has single crossover between the upstream homology arm of the malR gene and the genomic DNA of Bacillus licheniformis DW2, and also selecting the positive single crossover binder strain that has single crossover between the downstream homology arm of the malR gene and the genomic DNA of Bacillus licheniformis DW2; mixed culturing both in a 37° C. culturing medium absent of kanacillin, transferring and culturing for several times; and obtaining a malR-knockout Bacillus licheniformis DW2ΔmalR by PCR screening;

wherein, Bacillus licheniformis DW2 was deposited in the China Center for Type Culture Collection (CCTCC) in Wuhan on Oct. 12, 2011, and the deposit number is CCTCC NO: M2011344.

The malR gene in a genomic DNA sequence of the Bacillus licheniformis DW2 is shown in SEQUENCE LISTING.

The inventors have tried for the first time to construct malR-knockout Bacillus licheniformis DW2ΔmalR wherein malR is a gene responsible for transcriptional carbon metabolism transcription factor malR, and thereby successfully obtaining a malR-knockout Bacillus licheniformis strain. Therefore, the present invention provides a new strategy for increasing the yield of Bacitracin.

A second object of the present invention is to obtain a malR-knockout Bacillus licheniformis DW2ΔmalR based on the above method for constructing malR-knockout Bacillus licheniformis.

A third object of the present invention is the use of the malR-knockout Bacillus licheniformis DW2ΔmalR in the production of Bacitracin. Said use comprises the following steps: A. Seeding fermentation; B. Producing fermentation.

A culturing medium for the seeding fermentation is as follows: 6-10 g/L peptone, 2-6 g/L yeast extract powder, 6-10 g/L sodium chloride, pH 7.0~7.2.

A culturing medium for the producing fermentation is as follows: 60-100 g/L soybean meal; 15-40 g/L corn starch; 4-8 g/L $CaCO_3$ and 0.5-2 g/L $(NH_4)_2SO_4$.

Compared with Bacillus licheniformis DW2, the malR-knockout Bacillus licheniformis DW2ΔmalR constructed according to the present invention achieves an increase of more than 23% with respect to the yield of Bacitracin. Studies according to the present invention also show that: knockout of the malR gene for carbon metabolism transcription factor MalR from the genomic DNA of Bacillus licheniformis DW2 is a very effective method to increase the yield of Bacitracin.

Figure 1:
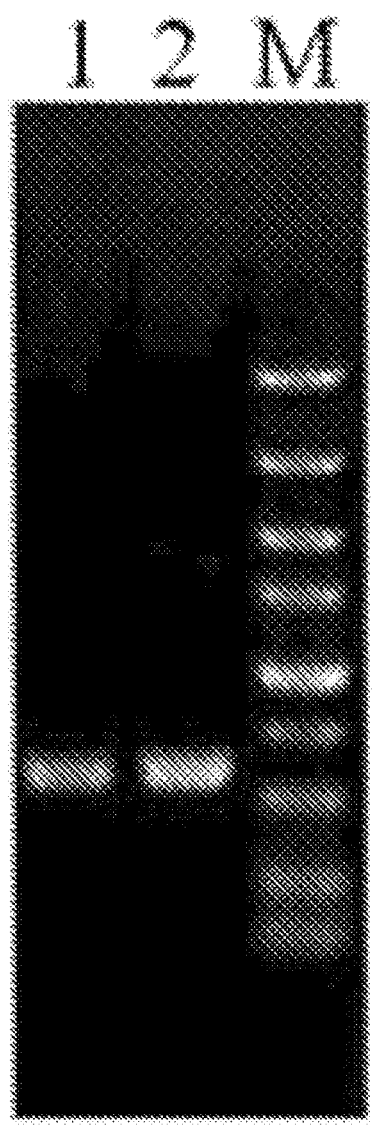
FIG. 1 is an agarose gel image of the upstream homology arm of the malR gene and the downstream homology arm of the malR gene obtained in step 1; wherein lane M is the DNA marker, lane 1 is the upstream homology arm of the malR gene, and lane 2 is the downstream homology arm of the malR gene.
Figure 2:
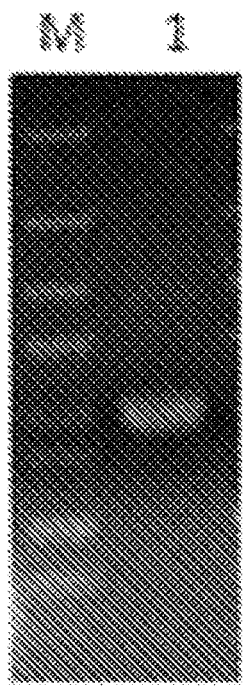
FIG. 2 is an agarose gel image of the target gene segment obtained in step 2; where lane M is a DNA marker, and lane 1 is the target gene segment obtained in step 2.
Figure 3:
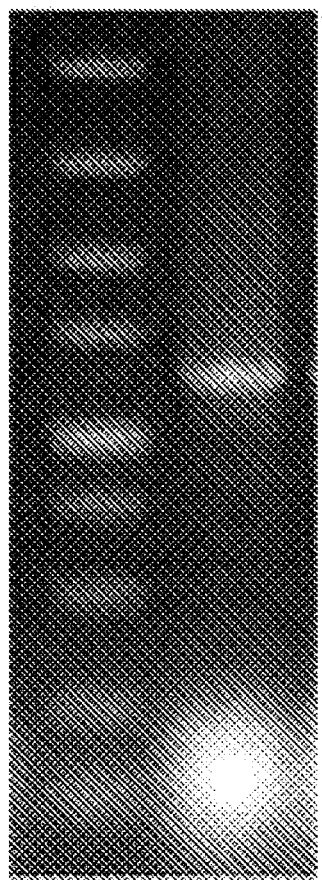
FIG. 3 is a colony PCR verification diagram of the knockout plasmid T2(2)ΔmalR obtained in step 5; wherein, lane M is the DNA marker, and lane 1 is the band of colony PCR verification of the knockout plasmid T2(2)ΔmalR.
Figure 4:
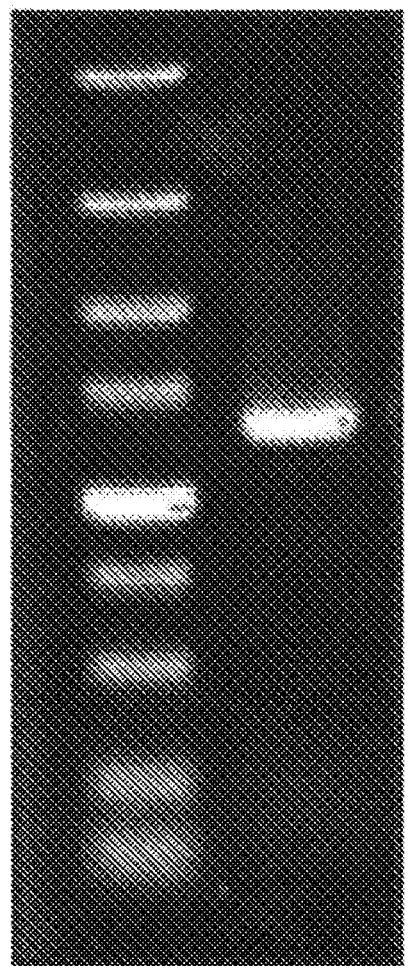
FIG. 4 is a colony PCR verification diagram of the positive transformant strain obtained in step 6, wherein lane M is the DNA marker, and lane 1 is a verification band of the positive transformant strain.
Figure 5:
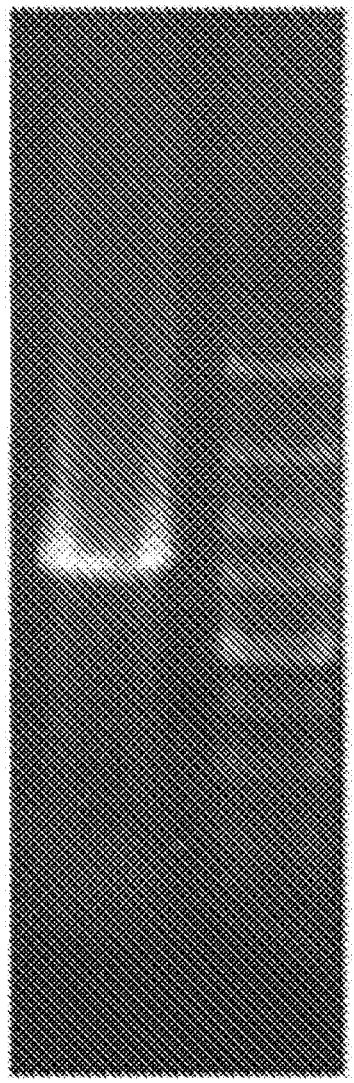
FIG. 5 is a verification band of malR-knockout *Bacillus licheniformis* DW2ΔmalR obtained in step 8, wherein lane M is the DNA marker, and lane 1 is the verification band of the malR-knockout *Bacillus licheniformis* DW2ΔmalR.

In the above figures, molecular weights corresponding to the respective bands from top to bottom of the DNA marker lane are: 5000 bp, 3000 bp, 2000 bp, 1500 bp, 1000 bp, 750 bp, 500 bp, 250 bp, and 100 bp.

DETAILED DESCRIPTION OF THE INVENTION

A preferred embodiment of the present invention is further described in detail below with reference to the accompanying drawings.

A method for constructing malR-knockout (malR is a transcription gene for carbon metabolism transcription factor MalR) *Bacillus licheniformis* strain, comprising the following steps:

(1) using genomic DNA of *Bacillus licheniformis* DW2 as a template, obtaining an upstream homology arm of the malR gene and a downstream homology arm of the malR gene by PCR (polymerase chain reaction) amplification;

(2) connecting the upstream homology arm of the malR gene and the downstream homology arm of the malR gene by overlap extension PCR to obtain a target gene segment;

(3) performing double digests of the target gene segment by XbaI and BamHI restriction enzymes to obtain a digested gene segment;

(4) preparing plasmid T2(2)-ori, and performing double digests of the plasmid T2(2)-ori by XbaI and BamHI restriction enzymes to obtain a linear plasmid segment;

(5) ligating the digested gene segment obtained in step (3) and the linear plasmid segment obtained step (4) by DNA ligase to obtain a knockout plasmid T2(2)-ΔmalR;

(6) transforming the knockout plasmid T2(2)-ΔmalR into *Bacillus licheniformis* DW2, and screening to obtain a positive transformant using kanacillin as a screening marker;

(7) after transferring and culturing the positive transformant for several times at 45° C., performing colony PCR to obtain positive single crossover binder strains that have single crossover between the upstream homology arm of the malR gene/the downstream homology arm of the malR gene and the genomic DNA of *Bacillus licheniformis* DW2;

(8) selecting the positive single crossover binder strain that has single crossover between the upstream homology arm of the malR gene and the genomic DNA of *Bacillus licheniformis* DW2, and also selecting the positive single crossover binder strain that has single crossover between the downstream homology arm of the malR gene and the genomic DNA of *Bacillus licheniformis* DW2; mixed culturing both in a 37° C. culturing medium absent of kanacillin, transferring and culturing for several times; and obtaining a malR-knockout *Bacillus licheniformis* DW2ΔmalR by PCR screening;

wherein, *Bacillus licheniformis* DW2 was deposited in the China Center for Type Culture Collection (CCTCC) having address at College of Life Sciences, Wuhan University, Wuhan 430072 deposited on Oct. 12, 2011, and the deposit (accession) number is CCTCC NO: M2011344. The taxonomic description is as follows:

Domain: Bacteria
Phylum: Firmicutes
Class: Bacilli
Order: Bacillales
Family: Bacillaceae
Genus: *Bacillus*
Species: *licheniformis*

The malR gene in a genomic DNA sequence of the *Bacillus licheniformis* DW2 is shown in SEQUENCE LISTING.

Said carbon metabolism transcription factor MalR was published in the GenBank of the National Center for Biotechnology Information (NCBI).

Detailed procedures of each step in said method for constructing malR-knockout *Bacillus licheniformis* strain are as follows:

1. Detailed procedures of said step 1 are as follows:
designing upstream homology arm primers (malR-F1, malR-R1) and downstream homology arm primers (malR-F2, malR-R2) of the malR gene according to gene sequence of the malR gene in a sequence of the genomic DNA of *Bacillus licheniformis* DW2; using the genomic DNA of *Bacillus licheniformis* DW2 as the template to perform PCR amplification using the upstream homology arm primers and the downstream homology arm primers of the malR gene to obtain an upstream homology arm segment of the malR gene and a downstream homology arm segment of the malR gene (the upstream homology arm segment of the malR gene is 515 bp; the downstream homology arm segment of the malR gene is 537 bp);

wherein the sequences of malR-F1, malR-R1, malF-F2 and malR-R2 are respectively being:
malR-F1 set forth in SEQ ID NO: 2
malR-R1 set forth in SEQ ID NO: 3
malR-F2 set forth in SEQ ID No: 4
malR-R2 set forth in SEQ ID No: 5

2. Detailed procedures of said step 2 are as follows:
using the upstream homology arm segment of the malR gene and the downstream homology arm segment of the malR gene as templates, and using the upstream homology arm primer malR-F1 and the downstream homology arm primer malR-R2 as primers; and then connecting the upstream homology arm of the malR gene and the downstream homology arm of the malR gene by overlap extension PCR to obtain the target gene segment 1052 bp;

3. Detailed procedures of said step 3 are as follows:
performing double digests of the target gene segment obtained in step 2 by XbaI and BamHI restriction enzymes to obtain the digested gene segment (1050 bp);

4. Detailed procedures of said step 4 are as follows:
preparing the plasmid T2(2)-ori (wherein the plasmid T2(2)-ori is constructed according to the following steps: 194-ori from plasmid pE194 kanamycin resistance gene from plasmid pDG780, and pUC-ori from plasmid pBluescript II SK(+)–X52328 are subject to reaction under PCR amplification, and then recovered and digested with restriction enzymes; connecting in sequential order the 194-ori the kanamycin resistance gene, and the pUC-ori. Reference literatures for the above construction method of plasmid T2(2)-ori: GUO, Xinghua, XIONG, Zhan et al. *Construction of Bacillus subtilis—E. coli multifunctional shuttle vector; Chinese Journal of Biotechnology* 7(3); 224-229, 1991 and PENG, Qingzhong, ZHANG, Weicai et al. *Construction of Bacillus pumilus—E. coli shuttle secretion expression vector; Chinese Journal of Biotechnology* 18(4):438-441, 2002), and performing double digests of the plasmid T2(2)-ori by XbaI and BamHI restriction enzymes to obtain a linear plasmid segment (4250 bp), wherein said XbaI and BamHI restriction enzymes are purchased from Beijing TransGen Biotech Co., Ltd.;

5. Detailed procedures of said step 5 are as follows:

ligating the digested gene segment obtained in step 3 and the linear plasmid segment obtained in step 4 by DNA ligase (in general, T4 DNA ligase) to obtain a ligation product; transforming the ligation product into *E. coli* DH5α by calcium chloride transformation, and then performing screening on a culturing medium having kanacillin resistance under a temperature of 37° C. to obtain a transformant, extracting plasmids from the transformant and performing colony PCR verification (primers used are: T2-F and T2-R); if PCR verification of the transformant results in an electrophoretic band appearing at 1304 bp, a knockout vector is constructed successfully, and the transformant is positive transformant (named as knockout vector T2(2)-ΔmalR);

6. Detailed procedures of said step 6 are as follows:

transforming the knockout vector T2(2)-ΔmalR into *Bacillus licheniformis* DW2, and then performing screening on a culturing medium having kanacillin resistance under a temperature of 37° C. to obtain a transformant, extracting plasmids from the transformant and performing colony PCR verification (primers used are: T2-F and T2-R); if PCR verification of the transformant results in an electrophoretic band appearing at 1304 bp, the knockout vector T2(2)-ΔmalR is successfully transformed into *Bacillus licheniformis* DW2, and the transformant is a positive transformant (i.e. the *Bacillus licheniformis* DW2 being transformed with the knockout vector T2(2)-ΔmalR);

wherein T2-F and T2-R have the following sequences respectively:

T2-F set forth in SEQ ID NO: 6;
T2-R set forth in SEQ ID NO: 7;

7. Detailed procedures of said step 7 are as follows:

transferring and culturing the positive transformant obtained in step (6) on a culturing medium having kanacillin resistance under a temperature of 45° C. for 3 times, 12 hours each time; and then performing colony PCR by using T2-F and ΔmalR-KYR as primers (or using T2-R and ΔmalR-KYF as primers) to detect single crossover strains; if a band with a length of 1819 bp or 2896 bp is being amplified, the single crossover strains are proved to exist;

wherein the sequences of ΔmalR-KYF and ΔmalR-KYR are respectively being:

ΔmalR-KYF set forth in SEQ ID NO: 8;
ΔmalR-KYR set forth in SEQ ID No: 9;

8. Detailed procedures of said step 8 are as follows:

selecting the single crossover strain showing the band length 1819 bp obtained in step 7 and the single crossover strain showing the band length 2896 bp obtained in step 7; transferring and mixed culturing both in a 37° C. culturing medium absent of kanacillin for several times; extracting transformant and performing colony PCR verification (primers used are: ΔmalR-KYF and ΔmalR-KYR); if PCR verification of the transformant results in an electrophoretic band appearing at 2003 bp, there is back mutation of the gene, and the transformant is *Bacillus licheniformis* DW 2; if an electrophoretic band appears at 1550 bp, the malR gene in the genomic DNA of DW2 is successfully knockout, and the transformant is a positive transformant; further verifying the positive transformant by DNA sequencing; thereby obtaining a double crossover malR-knockout strain (i.e. malR-knockout *Bacillus licheniformis* DW2ΔmalR).

The present invention also provides a malR-knockout *Bacillus licheniformis* DW2ΔmalR based on the above method for constructing malR-knockout *Bacillus licheniformis*.

The present invention also provides use of the malR-knockout *Bacillus licheniformis* DW2ΔmalR in the production of Bacitracin. Said use comprises the following step: A. Seeding fermentation; B. Producing fermentation.

Inventors of the present invention provide 14 embodiments concerning the steps of using the malR-knockout *Bacillus licheniformis* DW2ΔmalR in the production of Bacitracin. The following table 1 discloses a culturing medium for seeding fermentation and a culturing medium for producing fermentation respectively according to each of embodiment 1 to embodiment 14.

TABLE 1

| Embodiment | Culturing medium for seeding fermentation (pH 7.0-7.2) | | | Culturing medium for producing fermentation | | | |
|---|---|---|---|---|---|---|---|
| | Peptone (g/L) | Yeast extract powder (g/L) | Sodium chloride (g/L) | Soybean meal (g/L) | Corn starch (g/L) | $CaCO_3$ (g/L) | $(NH4)_2SO_4$ (g/L) |
| 1 | 6 | 2 | 8 | 80 | 30 | 4 | 0.5 |
| 2 | 8 | 5 | 8 | 80 | 30 | 4 | 0.5 |
| 3 | 8 | 6 | 8 | 80 | 30 | 4 | 0.5 |
| 4 | 8 | 3 | 6 | 80 | 30 | 4 | 0.5 |
| 5 | 9 | 3 | 8 | 80 | 30 | 4 | 0.5 |
| 6 | 10 | 3 | 8 | 80 | 30 | 4 | 0.5 |
| 7 | 8 | 3 | 8 | 80 | 15 | 4 | 0.5 |
| 8 | 8 | 3 | 8 | 80 | 40 | 4 | 0.5 |
| 9 | 8 | 3 | 10 | 80 | 30 | 6 | 0.5 |
| 10 | 8 | 3 | 8 | 80 | 30 | 8 | 0.5 |
| 11 | 8 | 3 | 8 | 80 | 30 | 4 | 1 |
| 12 | 8 | 3 | 8 | 60 | 30 | 4 | 2 |
| 13 | 8 | 3 | 8 | 80 | 30 | 4 | 0.5 |
| 14 | 8 | 3 | 8 | 100 | 30 | 4 | 0.5 |

All of the above embodiments use the malR-knockout *Bacillus licheniformis* DW2-ΔmalR strain obtained according to the construction method provided by the present invention. The specific steps of seeding fermentation are: firstly, activating the *Bacillus licheniformis*, which comprises transferring the *Bacillus licheniformis* from a glycerin tube at a volume percentage of 1% to a culturing medium containing 5 ml lysogeny broth (LB), and then culturing for 10-14 hours under 180-300 r/min and 37° C.; and next, transferring the resulting bacterial liquid containing the activated *Bacillus licheniformis* at a volume percentage of 1% into a culturing medium for seeding fermentation (in embodiments 1-14, the culturing media for seeding fermentation are liquid culturing media; if solid culturing media are required, it is only required to add 15-18 g/L agar into the original culturing media for seeding fermentation (i.e. the liquid culturing media)), and then culturing at 180-300 r/min and 37° C. for 10-12 hours to obtain a bacterial liquid for seed culturing. Specific steps of producing fermentation are: adding 25-150 mL of culturing medium for producing fermentation into a 500 mL Erlenmeyer flask, and then transferring the bacterial liquid for seeding fermentation at an amount of 2% (volume percentage) and then culturing for 48 hours for fermentation under revolution speed of 180~300 r/min and temperature 37° C. to obtain a bacterial solution for producing fermentation. Said specific steps for seeding fermentation and producing fermentation are known in the prior art.

The inventors uses high performance liquid chromatography (HPLC) method to determine the amount of Bacitracin in the bacterial liquid for producing fermentation in each of the above embodiments. The specific conditions for determination comprise the following: using Agilent 1200 liquid chromatography equipment for determination; chromatographic columns being Hypersil BDS C18 (5 μm, 4.6 mm×250 mm); mobile phase being A:B=35:65 (Phase A: mixing evenly 100 mL of phosphate buffer solution of pH 6.0 into 300 mL of water; Phase B: mixing evenly 520 mL methanol and 40 mL acetonitrile); flow rate: 1.0 mL/min; column temperature 30° C.; UV detector wavelength: 254 nm: sample amount 20 μL. The yield of Bacitracin in the bacterial liquid for producing fermentation is calculated according to a standard curve of producing standard product of Bacitracin (see Table 2).

TABLE 2

| Embodiment | Yield of Bacitracin according to the present invention (U/mL) | Control Group (yield of Bacitracin produced from bacterial liquid for producing fermentation obtained through DW2) (U/mL) | Percentage incease of yield of Bacitracin compared with using DW2 |
| --- | --- | --- | --- |
| 1 | 918.53 | 746.58 | 23 |
| 2 | 923.41 | 744.32 | 24 |
| 3 | 917.89 | 740.43 | 25 |
| 4 | 984.53 | 786.42 | 25 |
| 5 | 971.04 | 770.12 | 26 |
| 6 | 930.78 | 744.89 | 25 |
| 7 | 897.01 | 700.54 | 28 |
| 8 | 1002.32 | 764.53 | 31 |
| 9 | 965.10 | 777.74 | 24 |
| 10 | 888.43 | 720.54 | 23 |
| 11 | 952.17 | 754.75 | 26 |
| 12 | 984.12 | 793.32 | 24 |
| 13 | 937.26 | 750.16 | 25 |
| 14 | 1042.53 | 811.26 | 28 |

As shown in Table 2, under the same conditions for seeding fermentation and producing fermentation, there is a significant increase in the potency of Bacitracin (by more than 23%) in the bacterial liquid for producing fermentation using the malR-knockout *Bacillus licheniformis* DW2-ΔmalR according to the present invention, compared with using simply *Bacillus licheniformis* DW2 in the prior art. Therefore, there is a significant value of use of the present invention in respect of increasing the yield of Bacitracin from *Bacillus licheniformis*.

The invention claimed is:

1. A method of making a malR-knockout *Bacillus licheniformis*, the method comprising the steps of:
   (1) using genomic DNA of *Bacillus licheniformis* DW2 as a template, obtaining an upstream homology arm of the malR gene and a downstream homology arm of the malR gene by polymerase chain reaction (PCR) amplification;
   (2) connecting the upstream homology arm of the malR gene and the downstream homology arm of the malR gene by overlap extension PCR to obtain a target gene segment;
   (3) performing double digests of the target gene segment by XbaI and BamHI restriction enzymes to obtain a digested gene segment;
   (4) preparing plasmid T2(2)-ori, and performing double digests of the plasmid T2(2)-ori by XbaI and BamHI restriction enzymes to obtain a linear plasmid segment;
   (5) ligating the digested gene segment obtained in step 3 and the linear plasmid segment obtained in step 4 by DNA ligase to obtain a knockout plasmid T2(2)-ΔmalR;
   (6) transforming the knockout plasmid T2(2)-ΔmalR into *Bacillus licheniformis* DW2, and screening to obtain a positive transformant using kanacillin as a screening marker;
   (7) after transferring and culturing the positive transformant for several times at 45° C., performing colony PCR to obtain positive single crossover binder strains that have single crossover between the upstream homology arm of the malR gene/the downstream homology arm of the malR gene and the genomic DNA of *Bacillus licheniformis* DW2;
   (8) selecting the positive single crossover binder strain that has single crossover between the upstream homology arm of the malR gene and the genomic DNA of *Bacillus licheniformis* DW2, and also selecting the positive single crossover binder strain that has single crossover between the downstream homology arm of the malR gene and the genomic DNA of *Bacillus licheniformis* DW2; mixed culturing both in a 37° C. culturing medium absent of kanacillin, transferring and culturing for several times; and obtaining a malR-knockout *Bacillus licheniformis* DW2ΔmalR by PCR screening;
   wherein, *Bacillus licheniformis* DW2 is deposited in the China Center for Type Culture Collection (CCTCC) in Wuhan on Oct. 12, 2011 having a deposit number CCTCC NO: M2011344;
   wherein the malR genomic DNA sequence of the *Bacillus licheniformis* DW2 comprises SEQ ID NO: 1.

2. The method according to claim 1, wherein bacitracin is produced by culturing said malR-knockout *Bacillus licheniformis* in a culture medium for seeding fermentation and producing fermentation.

3. The method according to claim 1, wherein the culturing medium for the seeding fermentation comprises 6-10 g/L peptone, 2-6 g/L yeast extract powder, 6-10 g/L sodium chloride, pH 7.0~7.2.

4. The method according to claim 1, wherein the culturing medium for the producing fermentation comprises 60-100 g/L soybean meal; 15-40 g/L corn starch; 4-8 g/L $CaCO_3$ and 0.5-2 g/L $(NH_4)_2SO_4$.

* * * * *